Figure 1:
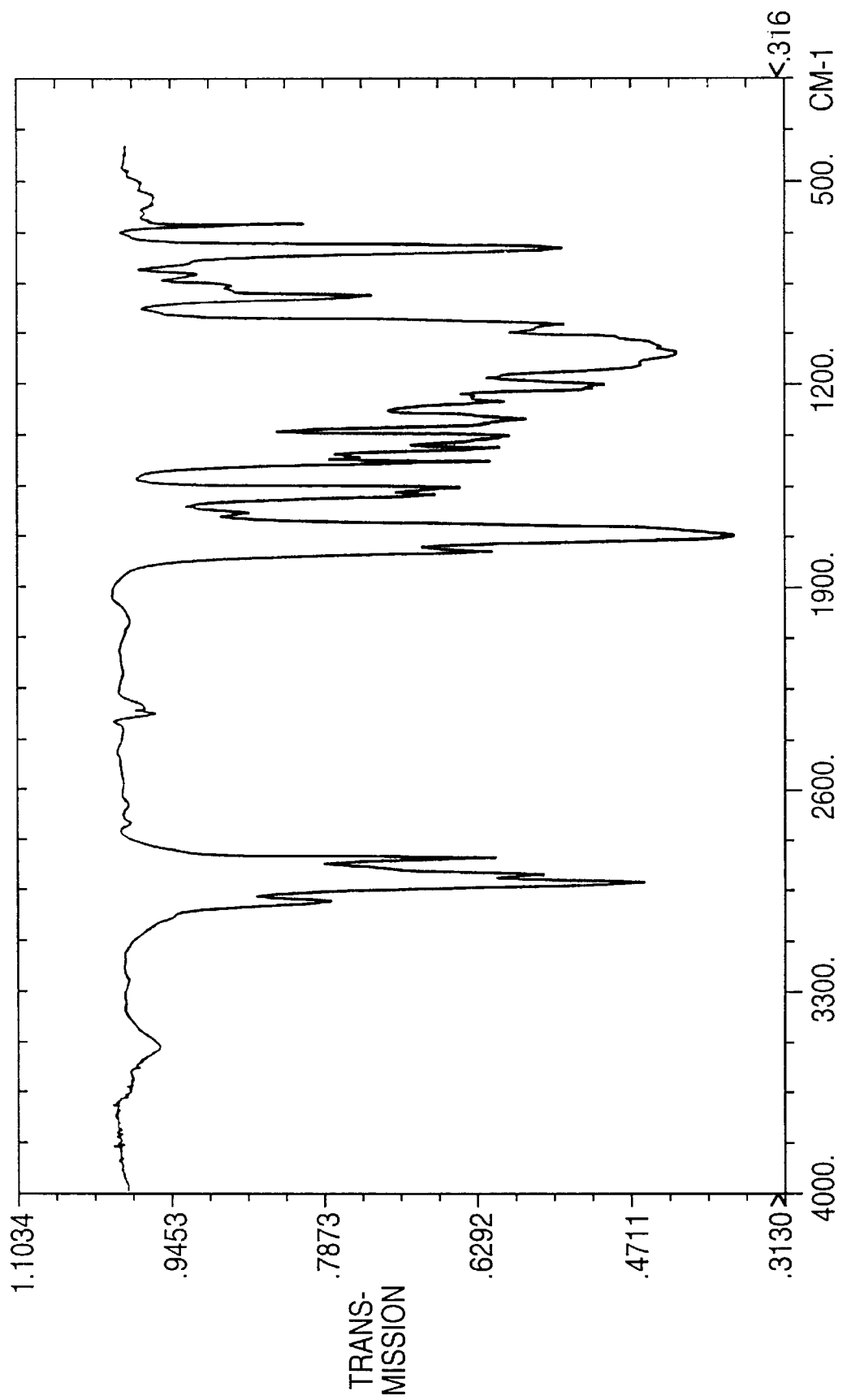
Figure 2:
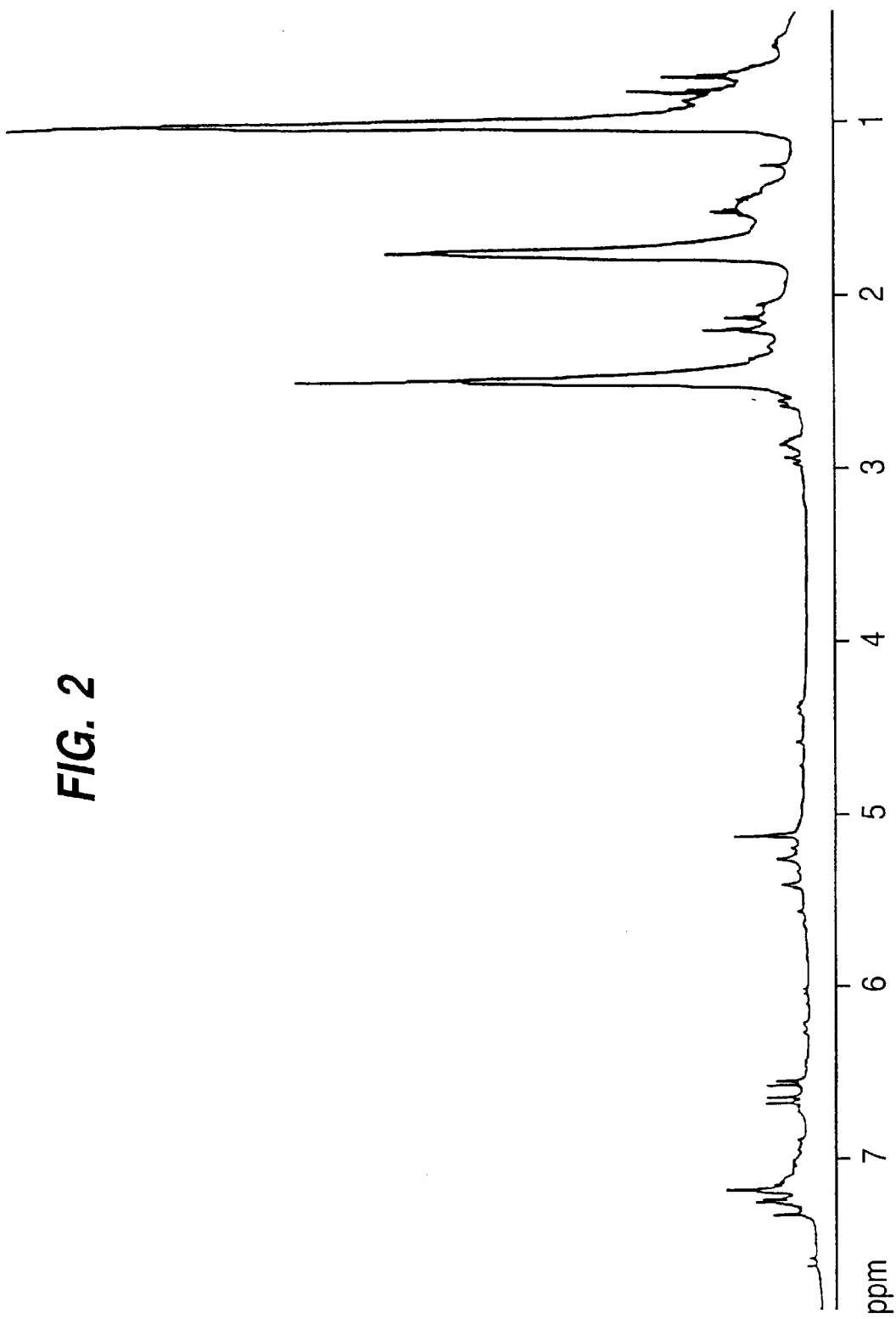
Figure 3:
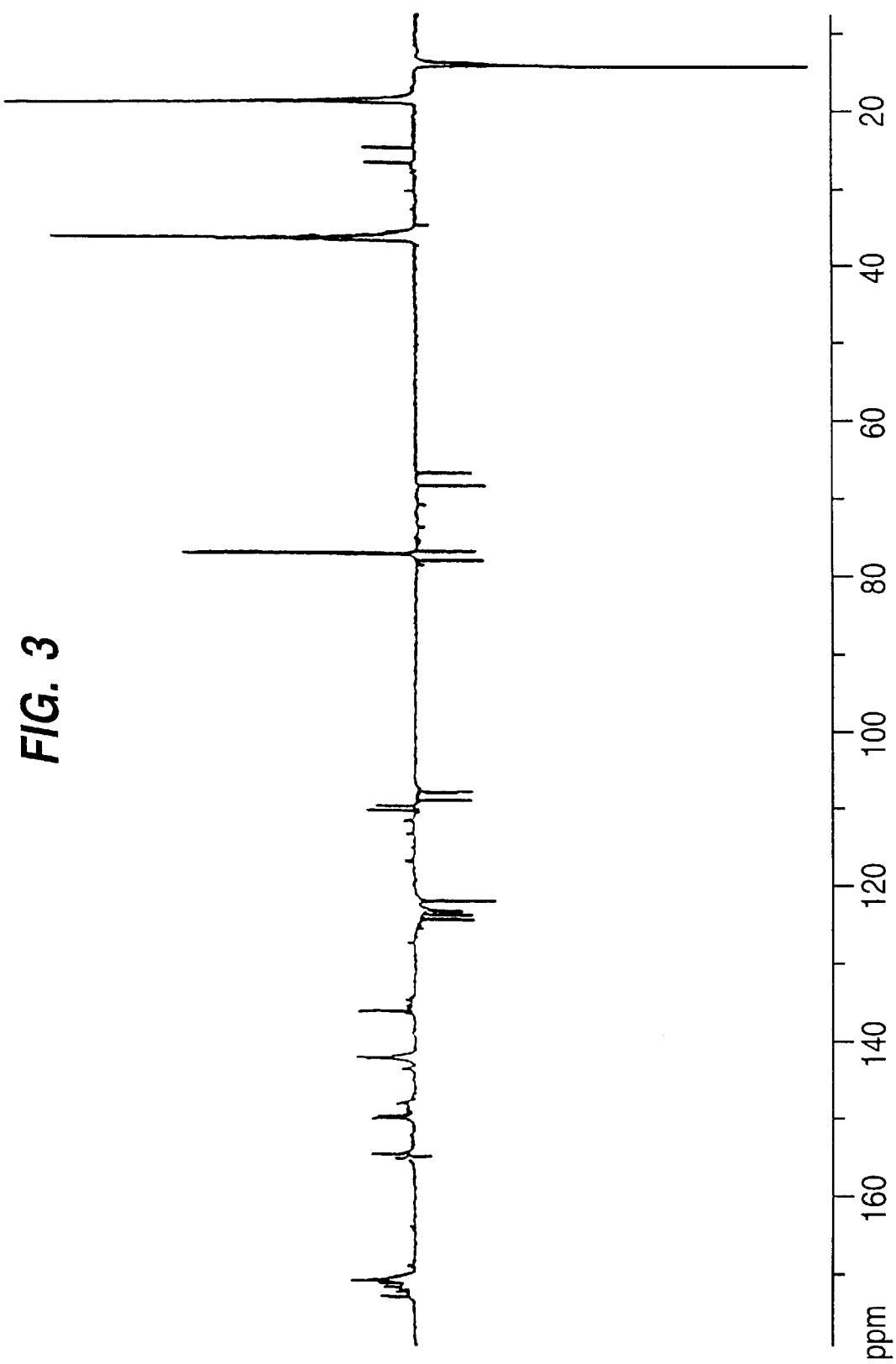
Figure 4:
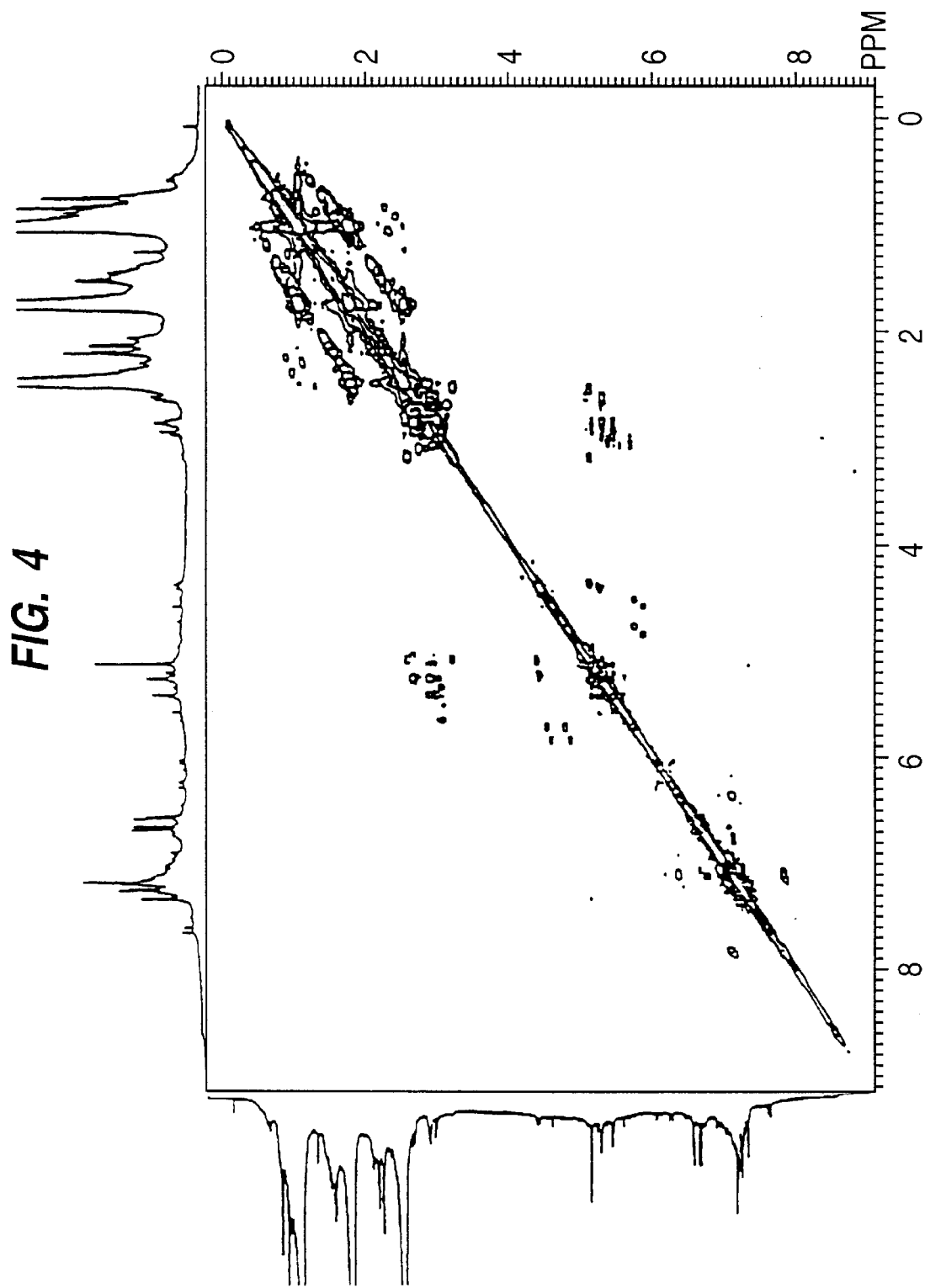
Figure 5:
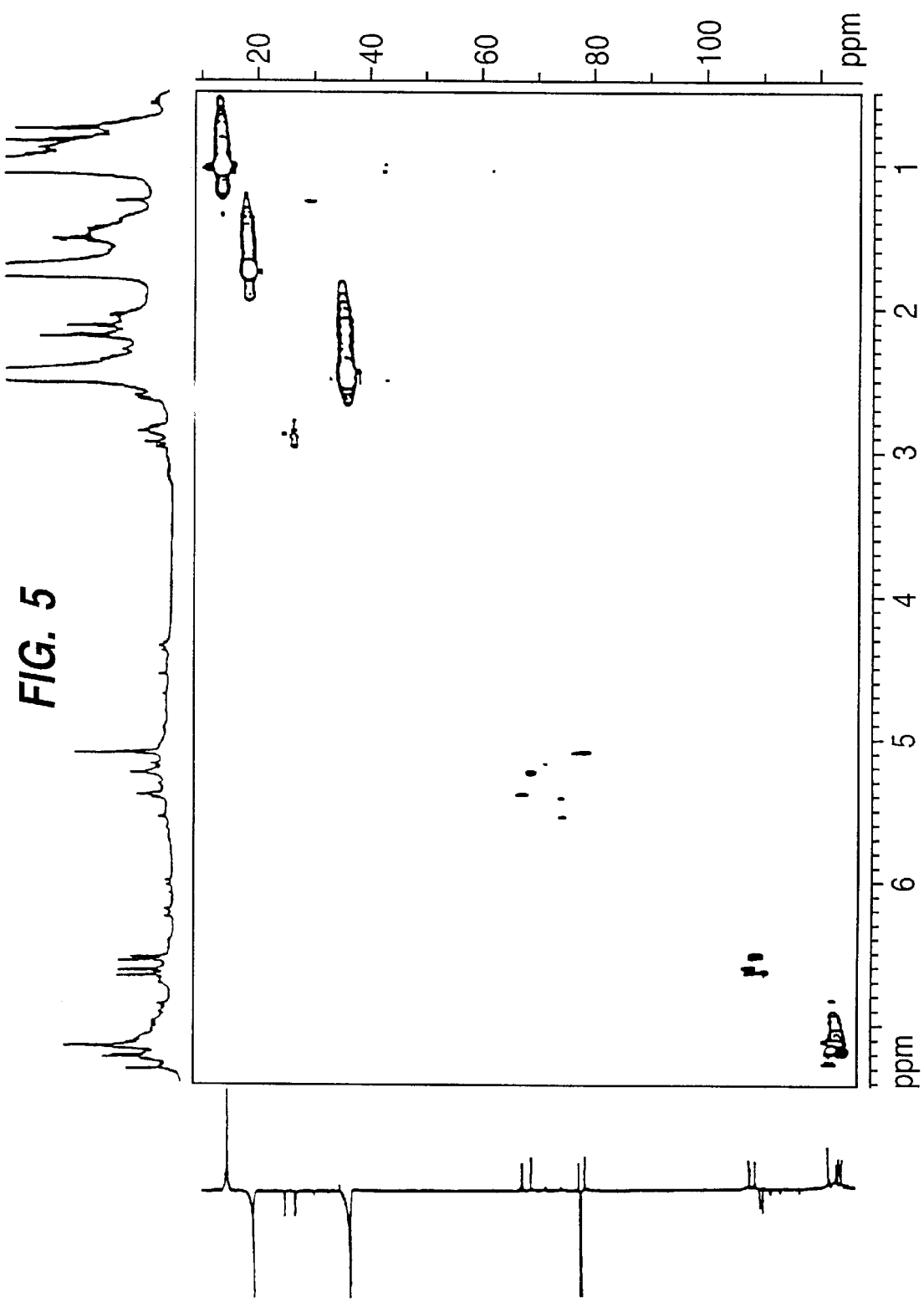
Figure 6:
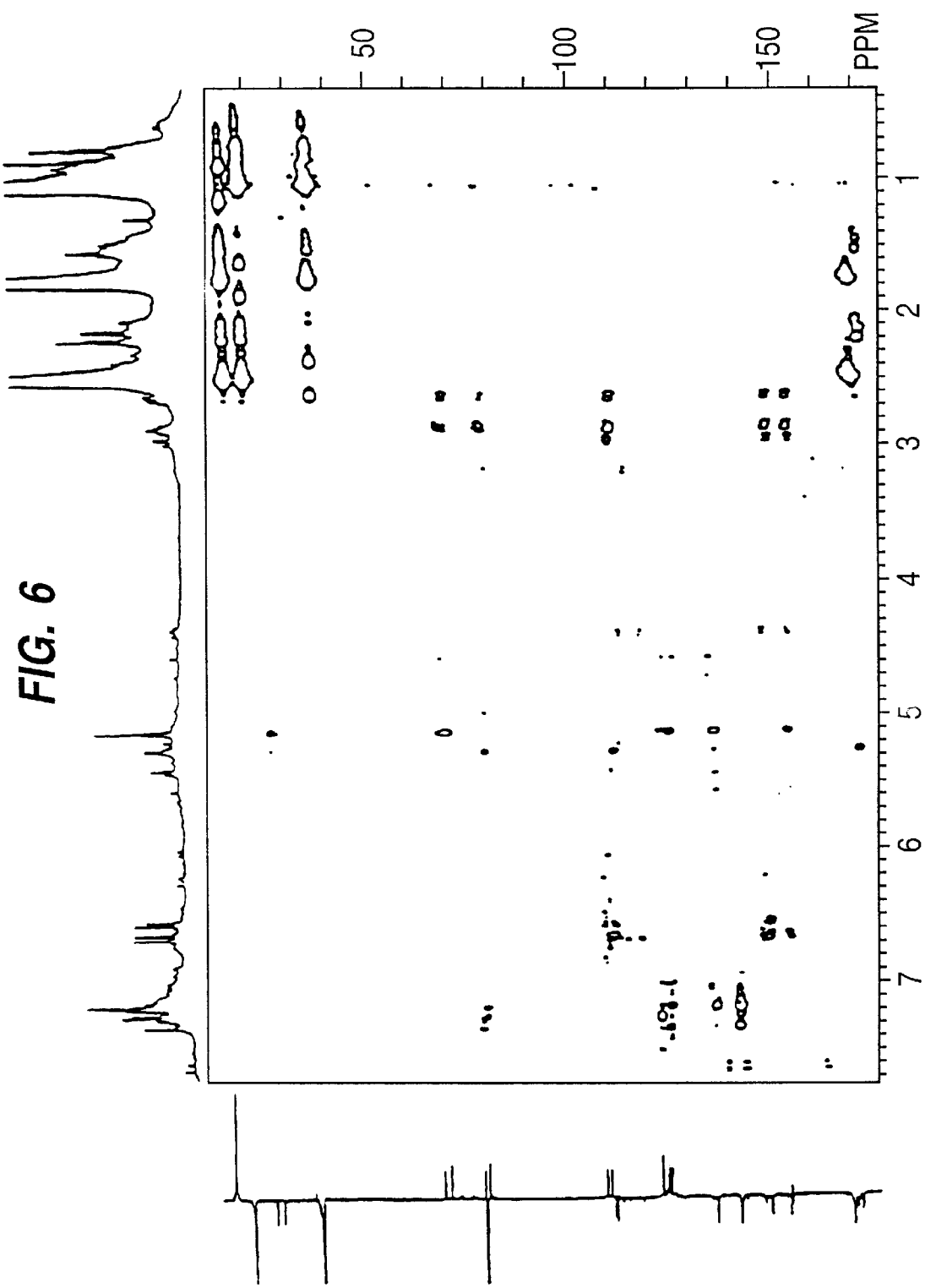

United States Patent [19]
Vercauteren et al.

[11] Patent Number: 5,844,061
[45] Date of Patent: Dec. 1, 1998

[54] POLYPHENOL DERIVATIVE COMPOSITIONS AND PERPARATION THEREOF

[75] Inventors: Joseph Vercauteren, Pessac; Jean-Frédéric Weber; Jean-Louis Bisson, both of Bordeaux; Jean Bignon, Nantes, all of France

[73] Assignee: Berkem, Gardonne, France

[21] Appl. No.: 557,179

[22] PCT Filed: Jun. 14, 1994

[86] PCT No.: PCT/FR94/00712

§ 371 Date: Dec. 13, 1995

§ 102(e) Date: Dec. 13, 1995

[87] PCT Pub. No.: WO94/29404

PCT Pub. Date: Dec. 22, 1994

[30] Foreign Application Priority Data

Jun. 14, 1993 [FR] France ................... 93 07140

[51] Int. Cl.$^6$ .................................................. C08G 18/32
[52] U.S. Cl. ..................... 528/86; 424/280.1; 424/283.1; 546/269; 546/270
[58] Field of Search ............................. 424/280.1, 283.1; 546/269, 270; 528/86

[56] References Cited

U.S. PATENT DOCUMENTS 4,166,861  9/1979  Bonati et al. ........................ 424/278
4,255,336  3/1981  Albert et al. ....................... 260/345.2
4,617,296  10/1986  Albert et al. ........................ 514/100

FOREIGN PATENT DOCUMENTS 1518003  1/1969  Germany .

OTHER PUBLICATIONS

Chemical Abstract "Constituents of Phanus spinota" 1992 Irizar et al.
Chemical Abstract Studies on the constituents of Ephedre 14. Validity of the oriental medicines 59. Structure of Mshusrrin C, a hypotensive principle of Ephedra roots.
French Search Report, Mar. 1, 1994, in French Priority Application No. 93 07140.
PCT Search Report for PCT FR94/00712 (with English translation).

(List continued on next page.)

Primary Examiner—Duc Truo
Attorney, Agent, or Firm—Staas & Halsey

[57] ABSTRACT

Polyphenol derivative compositions including oligomer or polymer esters containing N+2 monomer moieties, whose monomer moieties correspond to the following formula

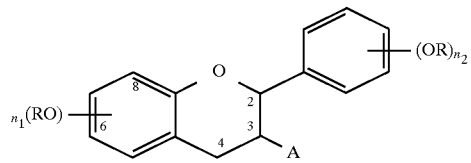

in which N is a number from 0 to 100, A represents a group —OR, a hydrogen atom or a substituent R, at least a majority of the substituents R represent a group —$COR_1$, $R_1$ is a saturated or unsaturated, linear or branched alkyl radical of at least two carbon atoms, or an aryl, aralkyl or aralkylene radical, a remainder of the substituents R is a hydrogen atom, an alkyl group, an acyl group —CO—$C_6H_2$—$(OH)_3$, a monosaccharide or a polysaccharide, and $n_1$ and $n_2$, which are identical to or different from each other, are numbers from 1 to 3, corresponding to the number of substitutions on a ring, and the diastereoisomers and the regioisomers of said monomer moieties, whereby the monomer moieties are connected by carbon—carbon bonds or by ether bridges between the rings which make up a flavan ring system.

32 Claims, 13 Drawing Sheets

OTHER PUBLICATIONS

English Abstract of JP A 1 233 277 (Mitsui Norin KK), Sep. 19, 1989.
English Abstract of JP A 4 190 774 (Kikkoman Corp.) Jul. 9, 1992.
English Abstract of JP A 56 095 182 (Noriinsho) Aug. 1, 1981.
English Abstract of JP A 1 268 683 (Mitsui Norin KK), Oct. 26, 1989.
English Abstract of JP A 5 163 131 (Kanebo) Jun. 29, 1993.
English Abstract of JP A 6 040 883 (Suzuyo) Feb. 15, 1994.
English Abstract of JP A 63 020 321 (Hitachi), Jan. 28, 1988.
Chemical Abstract, vol. 94, No. 11, Mar. 16, 1981, Columbus Ohio, Abstract No. 80196x, "Dimeric Procyanidins from Juniperus Sabina," p. 379, Colonne R.
Chemical Abstract, vol. 96, No. 26, Jun. 28, 1982, Columbus, Ohio, Abstract No. 223079r, Otsuka Hiroshi, "Studies on Anti–inflammatory agents. VI. Anti–inflammatory Constituents of Cinnamomum Sisboldii Meissn.", p. 358.
Eugen Muller ' Methoden der Organischen Chemie; Sauerstoffverbindungen III; (Houben–Weyl); 1952, Georg Thieme Verlag, Stuttgart, DE vierte Auflage, Band VIII, p. 559.

POLYPHENOL DERIVATIVE COMPOSITIONS AND PERPARATION THEREOF

The invention relates to novel polyphenol derivative compositions and to their preparation.

The invention relates more particularly to compositions containing polyhydroxylated derivatives of flavan and especially of 3-flavanol.

It is recalled that the flavan ring system corresponds to the structure (x):

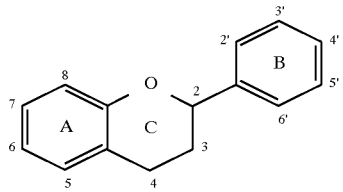

(x)

the 3-flavanols possessing an —OH group in the 3-position.

Flavanols, polyhydroxylated on the benzene rings, may be obtained by extraction from various plant sources such as various species of pine, green tea or grape vine. The crude extracts isolated are formed of complex mixtures comprising monomers and polymers, more particularly oligomers ranging from diners and, most generally, up to decamers.

Industrial extraction processes are directed towards providing fractions consisting mainly of oligomers. These fractions will be referred to indiscriminately hereinbelow as flavanol oligomers or as procyanolide oligomers, abbreviated to OPC.

The phenol groups present on the flavanol moieties impart to these OPCs anti-radical and antioxidizing properties which offer a potential advantage for numerous applications.

Certain OPC extracts are used therapeutically as vascular protectors or in cosmetics.

The practical and wider use of these products is sometimes hampered by the problem of their instability, due to the presence of free phenolic groups.

In general, phenols are products which oxidize spontaneously on contact with atmospheric oxygen and/or in the presence of light, by involving a radical mechanism which may be represented by the following equation:

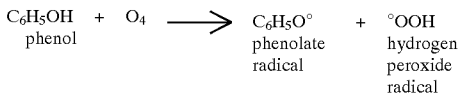

C$_6$H$_5$OH + O$_4$ ⟶ C$_6$H$_5$O° + °OOH
phenol       phenolate   hydrogen
         radical    peroxide
              radical As the phenolate radical is stabilized by the resonance effect, radical derivatives of the following type are formed:

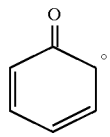

which may then undergo ortho or para coupling to give condensation products of the following types:

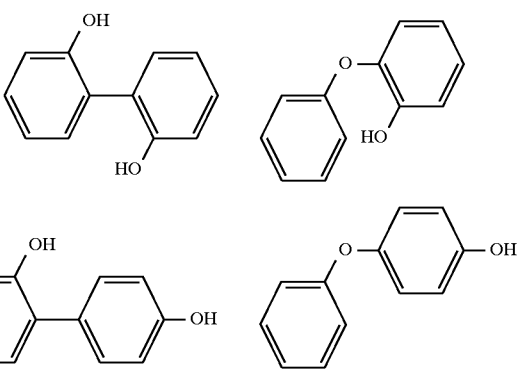

The polyphenol derivatives which follow such a mechanism give radical condensation products. When rearomatization cannot take place, products of quinone type add to these derivatives. This set of compounds is responsible for the appearance of red-brown colors, which are incompatible with certain applications.

Furthermore, OPCs are water-soluble products, which poses a problem of compatibility with a good number of excipients used generally in the abovementioned applications, these excipients having, on the contrary, liposoluble properties.

The search for means which make it possible to impart satisfactory stability to the polyhydroxylated derivatives and in particular to OPCS, and at the same time to render them liposoluble, has led the inventors to develop a technique for the protection of the free —OH groups by esterification under specific conditions.

The aim of the invention is thus to provide highly stable polyphenol derivative compositions.

The invention is also directed towards providing a process for the esterification of the phenol functions of these compositions, which process is easy to carry out and may be exploited on the industrial scale.

The invention is also directed towards the exploitation of the anti-radical and anti-oxidizing properties of these compositions in various fields, in particular in therapy, in cosmetics and in dietetics.

The compositions of the invention are characterized in that they mainly contain oligomers or polymers whose monomer moieties correspond to the formula (I):

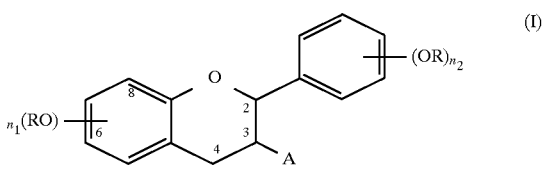

(I)

in which

A represents a group —OR, a hydrogen atom or a substituent R, at least the majority of the substituents R represent a group —COR$_1$, R$_1$ being a saturated or unsaturated, linear or branched alkyl radical of at least two carbon atoms, or an aryl, aralkyl or aralkylene radical, the other substituent or substituents R which do not represent a group —COR$_1$ being a hydrogen atom, an alkyl group, an acyl group —CO—C$_6$H$_2$—(OH)$_3$, a monosaccharide or a polysaccharide, and n$_1$ and n$_2$, which are identical to or different from each other, are numbers from 1 to 3, corresponding to the number of substitutions on a ring, and the diastereoisomers and the regioisomers of these moieties, the monomer moieties being connected by carbon—carbon bonds or by ether bridges between the rings which make up the flavan ring system.

The compositions thus esterified are of great stability. They may be stored for at least 2 years under normal storage conditions (temperature of 10° to 22° C., in light-protective packaging, hygrometry 40–50%).

The oligomers or the polymers of these esters correspond more especially to the formula II:

N is a number from 0 to 100, and the corresponding diastereoisomers and regioisomers.

In one family of the invention, the bonds between the carbon atoms of the successive moieties are located between C-4 of one moiety and C-6 or C-8 of another moiety.

Another family furthermore comprises at least two moieties connected by an oxygen bridge. Corresponding products correspond to the formula III:

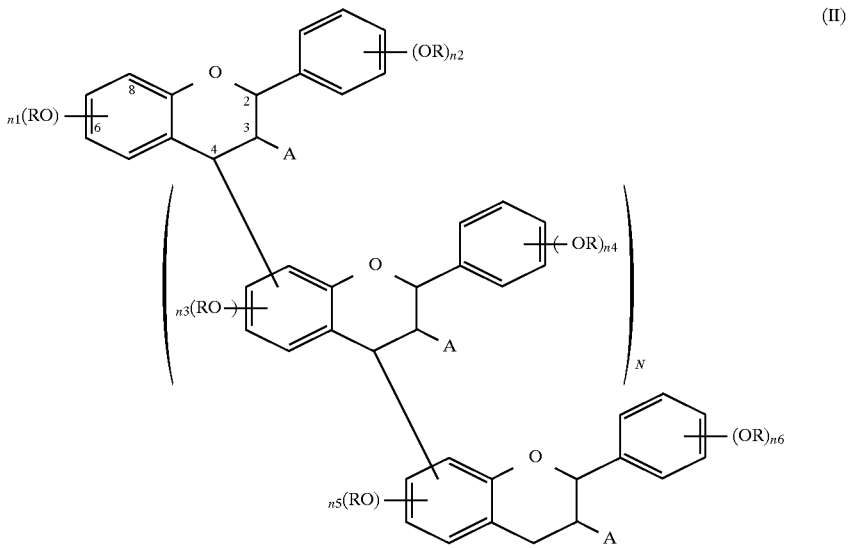

(II)

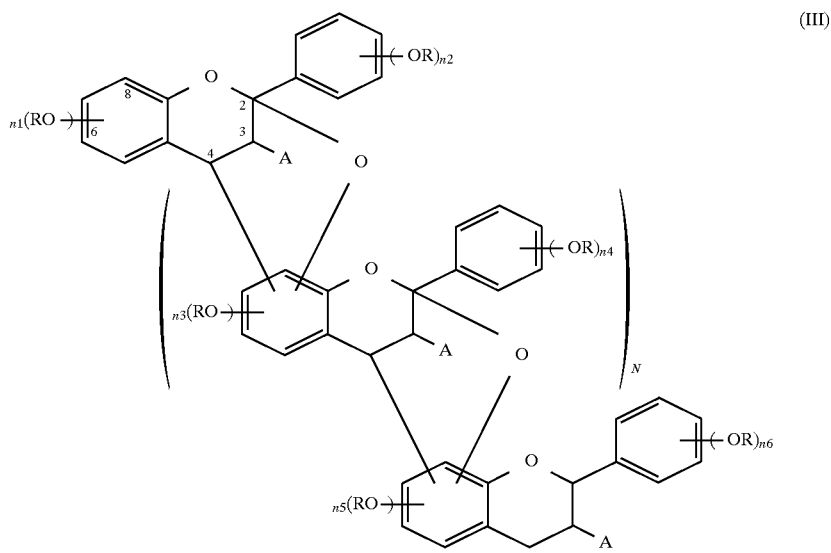

(III)

in which

A and R are as defined above, $n_1$ to $n_6$, which may be identical to or different from each other, are numbers from 1 to 3, representing the number of substituents on a benzene ring, and in which A, R, $n_1$ to $n_6$ and N are as defined above.

The monomer moieties are more especially connected by an ether bridge between C-2 of one moiety and one of the carbons $C_5$ to $C_8$ of the next moiety.

In one group of compositions of the invention, N is equal to 0 in the formula II or III above, the esters corresponding to dimers.

In another group, N is a number from 1 to 10.

In yet another group, N is greater than 10, in particular from 11 to 100.

In the compositions defined above, R1 advantageously represents a saturated or unsaturated fatty acid radical with, in this case, cis double bonds, this corresponding to the case which is the most common in natural products, or alternatively trans bonds, for products more particularly obtained synthetically or semi-synthetically.

Examples of fatty acids are given below. According to the conventional nomenclature, the number of carbon atoms C, then the number of double bonds, and the position of these double bonds is shown for each of them. The names of the fatty acids are given for the most standard.

These are the following acid radicals: butyric C4:0; valeric C5:0; hexanoic C6:0, sorbic C6:2(n-2); C8:0; C11:1; C11:2; lauric C12:0; C13:0; C13:2; C14:0; C15:0; C15:2; palmitic C16:0; C16:1(n-7); C16:2(n-4); C16:2(n-7); C16:3 (n-4); C16:4; C17:0; stearic C18:0; oleic C18:1(n-9); C18:1 (n-7), linoleic C18:2(n-6); linolenic C18:3(n-6); α linolenic C18:3(n-3); C18:4(n-3); C20:0; C20:1(n-9); C20:2(n-6); C20:3(n-6); C20:4(n-6); arachidonic C20:4(n-3); eicosapentaenoic C20:5(n-3); C22:0; C22:1; C22:1(n-5); C22:3(n-3); C22:4(n-6); C22:4(n-3); C22:5(n-3); C22:5(n-6); docosahexaenoic C22:6(n-3) and C24:1(n-9).

The fatty acid radicals of C16 and greater are more particularly preferred with a view to cosmetic applications. These fatty acids are advantageously extracted from microalgae.

According to another arrangement of the invention, $R_1$, represents an aryl group such as the phenyl radical.

According to yet another arrangement, $R_1$ represents an aralkyl or aralkylene group, the alkyl or alkylene group being more particularly a C1 to C8 group, especially a C1 to C4 group. Examples of aralkyl and aralkylene groups which will be mentioned are the benzyl and styryl groups.

The compositions defined in the various arrangements above include monomeric esters, as a mixture with the oligomeric esters and/or the polymeric esters which constitute the main products.

The invention is directed in particular towards flavanol derivative compositions. In these derivatives, the substituent A represents a group —OR, R being as defined above.

This preferably relates to esters of flavanol derivatives belonging to the catechol series.

In these esters, there are generally 5 oxygen-containing groups per flavanol moiety, and they occupy positions 3, 5, 7, 3' and 4'.

Reference will be made in the examples to peresters, to denote products in which all the —OH functions are esterified. These esters contain, where appropriate, an oxygen bridge between C-2 and one of the carbons $C_5$ to $C_8$.

Particularly preferred esters of flavanol derivatives are obtained from OPCs extracted from plant sources.

The plant materials most commonly used comprise various species of pine, grape vine and green tea.

In accordance with the invention, the compositions defined above are obtained by reacting corresponding phenolic compositions having at least one free —OH group with an acylating agent which is capable of providing the radical —$COR_1$, $R_1$ being as defined above, under conditions which allow the substitution of at least one free —OH group with an acyl radical —$COR_1$.

The acylating agent is advantageously chosen from acids $R_1COOH$ or derivatives of such acids, in particular acid chlorides $R_1COCl$, anhydrides $R_1COOR_1$ or esters $R_1COOR_2$, $R_2$ representing an aryl or $C_1$–$C_8$ alkyl radical.

When the acid is used as acylating agent, the reaction is advantageously performed in the presence of an acid-activating agent.

In the most conventional manner, this agent consists of dicyclohexylcarbodiimide, but other agents imparting the same activating effect may be used, such as tert-butyl chloroformate (for formation of a mixed anhydride).

The acylation reaction is carried out in the presence of a solvent which allows partial solubilization of the starting polyphenol compounds.

Suitable solvents are chosen from halogenated derivatives such as dichloromethane, chloroform or 1,2-dichloroethane, or an amine such as pyridine.

The reaction is preferably performed at room temperature.

The reaction with the acid chloride or anhydride may be performed, as a variant, in aqueous alkaline medium, according to the Schotten-Baumann reaction.

Thus, the polyphenol derivatives in aqueous phase at a pH of 7.5 to 12, in particular of 8 to 10, the acylating agent dissolved in an organic phase, and a phase transfer agent are placed together.

The organic phase in which the acylating agent is dissolved is advantageously an organochlorine solvent such as chloroform or dichloromethane.

Suitable phase transfer agents which will be mentioned are halides or hydroxides such as those of tetrabutylammonium or of tetrabutylphosphonium, hydrogen sulfates, for example tetrabutylammonium hydrogen sulfate, or alternatively benzyltriethylanmonium chloride.

The acylated derivatives obtained are separated from the reaction mixture and purified for the purposes of the applications envisaged. Suitable techniques comprise liquid-liquid extraction, chromatography and/or precipitation.

The starting polyhydroxylated compositions are advantageously commercial products. In the case of OPC, these products are obtained by extraction from plants. They are preferably purified fractions. A conventional extraction process is derived from that described in Patent FR 1,427,100 (PV No. 998,508) of 14 Dec. 1964. The OPCs are extracted from the plant material by saturated aqueous NaCl solution. Liquid-liquid extraction with ethyl acetate is then carried out, and the OPCs are then precipitated by adding excess chloroform. After filtration, the precipitate is taken up in ethyl acetate and subjected, if necessary, for the purposes of additional purification, to several cycles of reprecipitation with excess chloroform and uptake with ethyl acetate, the solvent being evaporated off at the end.

As a variant, these compositions are extracted from the plant material by water, followed by addition of NaCl. The impurities are precipitated and removed by filtration, followed by liquid-liquid extraction of the OPCs using ethyl acetate. The solvent is evaporated off and the residue taken up in water. After the steps of washing of the aqueous solution with chloroform, drying by spraying or uptake with ethyl acetate, the flavanol compositions are precipitated by adding excess chloroform, and are then filtered off and dried in the oven.

According to the extraction techniques used, the OPCs contain a sugar moiety as indicated above. This is a monosaccharide such as, for example, glucose or galactose, or polysaccharides formed from several of these monosaccharide units, which may be identical or different. These glycosylated derivatives are extracted from the plant material with water, an alcohol such as ethanol or methanol, or a water-acetone mixture (2/3). After washing with ethyl acetate, the extract is redissolved in aqueous solution. A liquid-liquid extraction with n-butanol is carried out, and the solvent is then removed by evaporation. The residue is subjected to countercurrent chromatographic purification or to chromatographic purification on Fractogel TSK HW40, Sephadex LH20, MCI CHP 20P gel or RP C18 silica gel.

The work carried out on the polyphenol derivative compositions of the invention has shown that the presence of the protective ester groups makes it possible to promote transportation of these compositions across biological membranes and locally to reach higher concentrations than with non-acylated compounds, according to the prodrug concept.

On contact with esterases, which are present in the majority of biological tissues and media, at least some of the ester protecting groups are removed, regenerating the staring phenol compounds and the acids $R_1COOH$. These compounds, in combination, exert their own activities, advantageously in a synergistic manner.

These advantageous properties are also accompanied by a considerable level of harmlessness, as demonstrated for the native polyphenol compositions and, in particular, for the flavanol compositions, as well as for the acids $R_1COOH$.

These compositions are thus particularly suitable for the development of pharmaceutical preparations.

The pharmaceutical preparations of the invention contain an effective amount of at least one phenolic composition as defined above, in particular of a flavanol composition, in combination with an inert pharmaceutical vehicle.

Advantageous pharmaceutical preparations contain these derivatives, alone or in combination with medicinal products which have a protective effect with respect to oxidation reactions. β-Carotene or vitamin E will be mentioned by way of example.

Given their anti-radical and anti-oxidizing properties, these pharmaceutical preparations may be used in particular in the following therapeutic indications: circulatory disorders, venolymphatic insufficiency, skin capillary fragility, disorders involving retinal circulation, hemorrhoidal crisis, solar erythema or erythema associated with the action of radiation, for example in the case of radiotherapy.

The pharmaceutical preparations of the invention may be administered orally.

Use may be made in particular of tablets, pills, lozenges, gelatin capsules or drops. These preparations advantageously contain from 50 to 200 mg of OPC equivalent, preferably from 100 to 150 mg, per dosage unit.

The compositions of the invention may also be administered transdermally using patches, or alternatively in the form of nasal spray.

In radiotherapy, these compositions may be used for the prevention of mucitis, in the form of a gel applied directly to the mucous membranes liable to be irradiated.

As a guide, the dosage which may be used in man, for the pathologies considered, corresponds to the following doses: phlebology and lymphology, 100 to 600 mg per day taken in two doses; ophthalmology, 100 to 400 mg per day; acute hemorrhoidal crisis: 200 mg to 1.2 g per day, radiotherapy: paste containing 1–5% of non-esterified polyphenol equivalent.

The anti-radical and anti-oxidizing properties of these compositions are also advantageously exploited for the development of cosmetic preparations.

In these preparations, the compositions are combined with vehicles which are suitable for external use. It will be noted that their liposoluble nature favors their incorporation into the pharmaceutical forms usually used in cosmetics.

For these applications, the preparations are in the form of a cream, a salve, an emulsion, a gel, liposomes or a lotion. They contain from 0.5 to 5% of active product.

According to another aspect of great value, the compositions of the invention may be used in dietetics. By virtue in particular of their anti-radical properties, they provide better storage of foods. Furthermore, they generally constitute a supply of vitamin factor, in particular of vitamin P, with flavanol compositions. They are thus advantageously added to drinks, for example to fruit juices, tonic drinks and to dairy products and derivatives such as butter.

They may also be used as they are in liquid form, or alternatively as granules or the like, as gels or in the form of a paste, for example incorporated into confectionery products such as fruit purees, confectionery sweets or chewing gums.

In these forms of application, the compositions of the invention may be mixed with products of interest such as vitamins and/or trace elements and/or fish oils rich in unsaturated fatty acids, such as halibut oil, mackerel oil or salmon oil.

Figure 7:
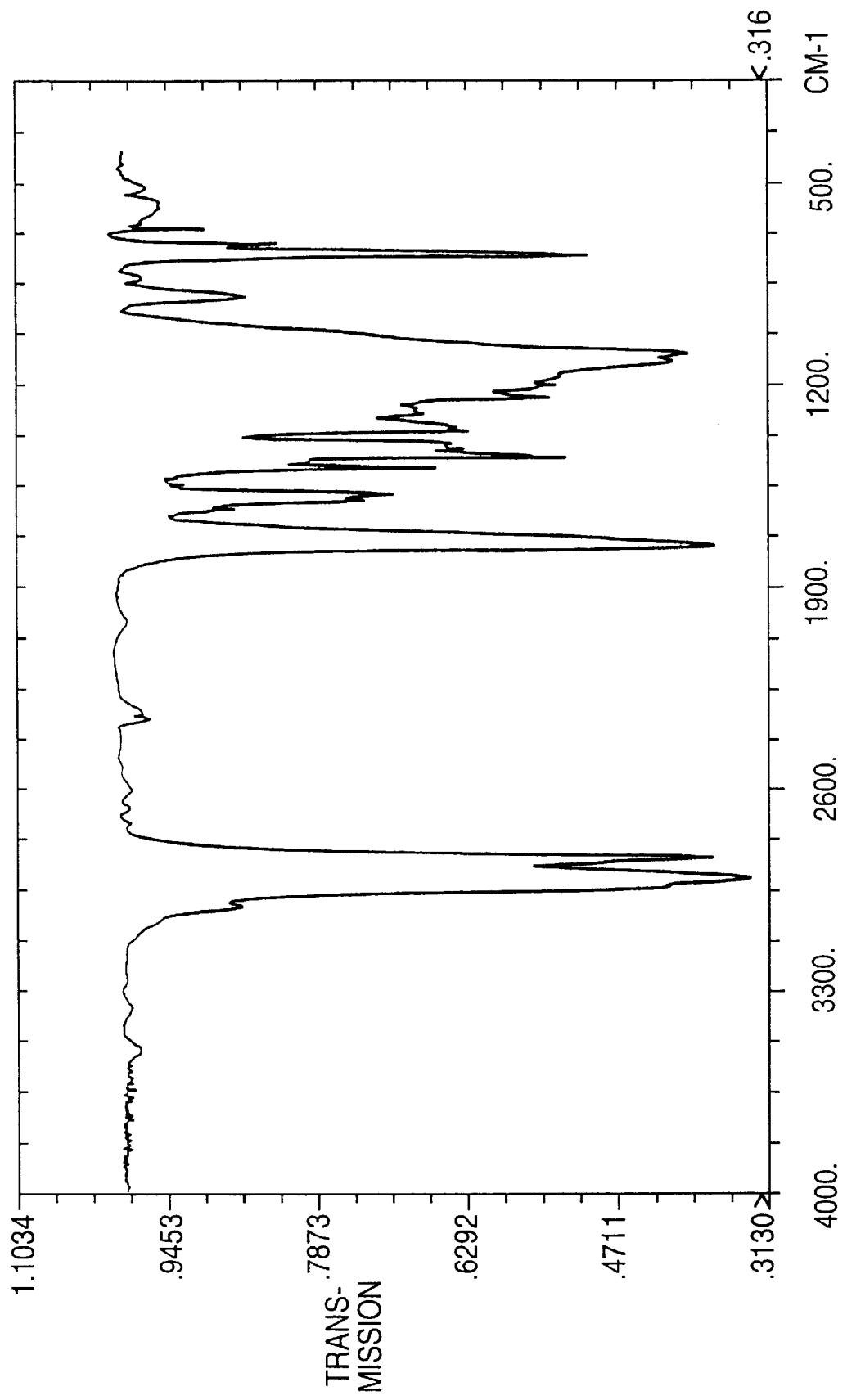
Figure 8:
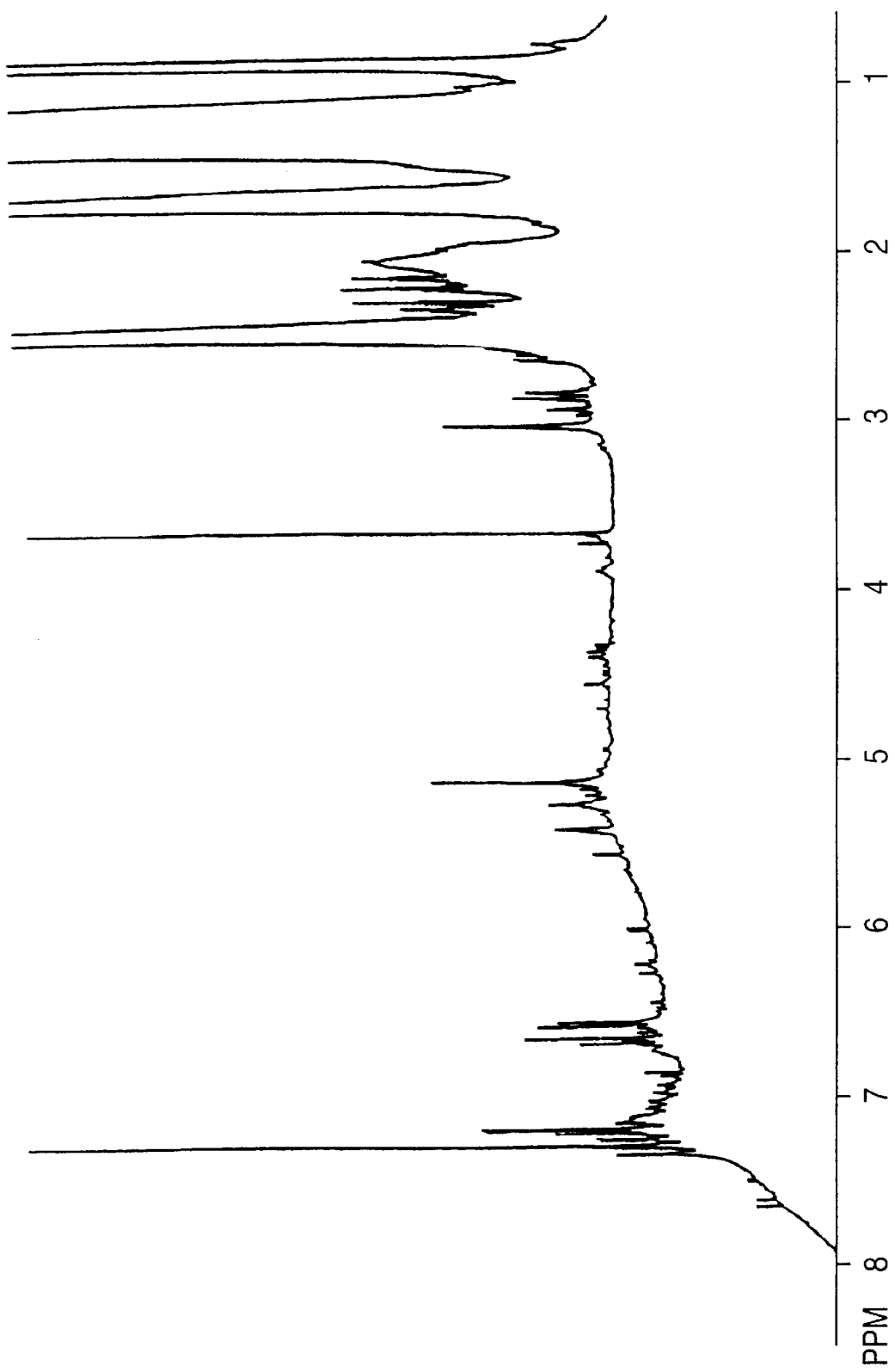
Figure 9:
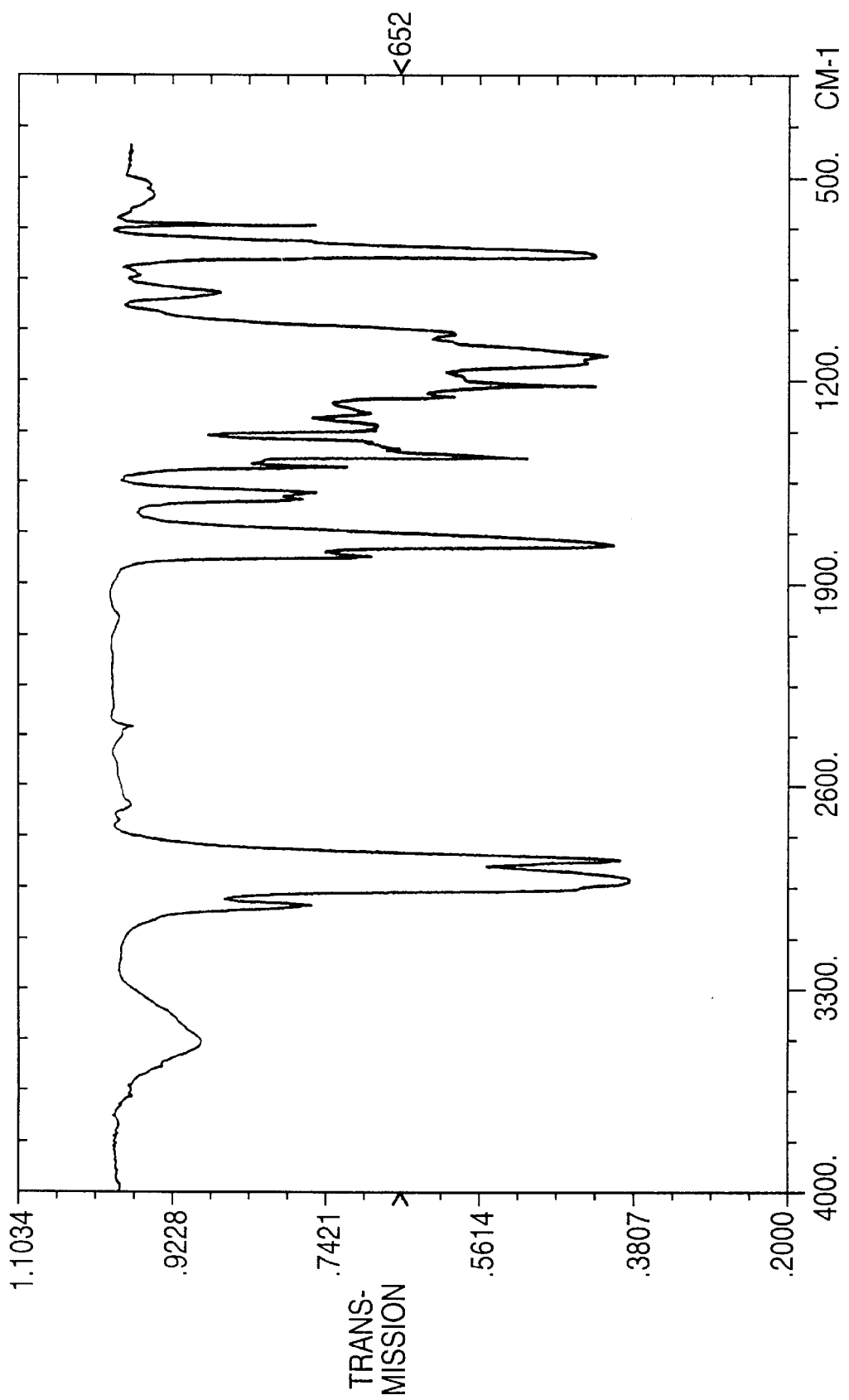
Figure 10:
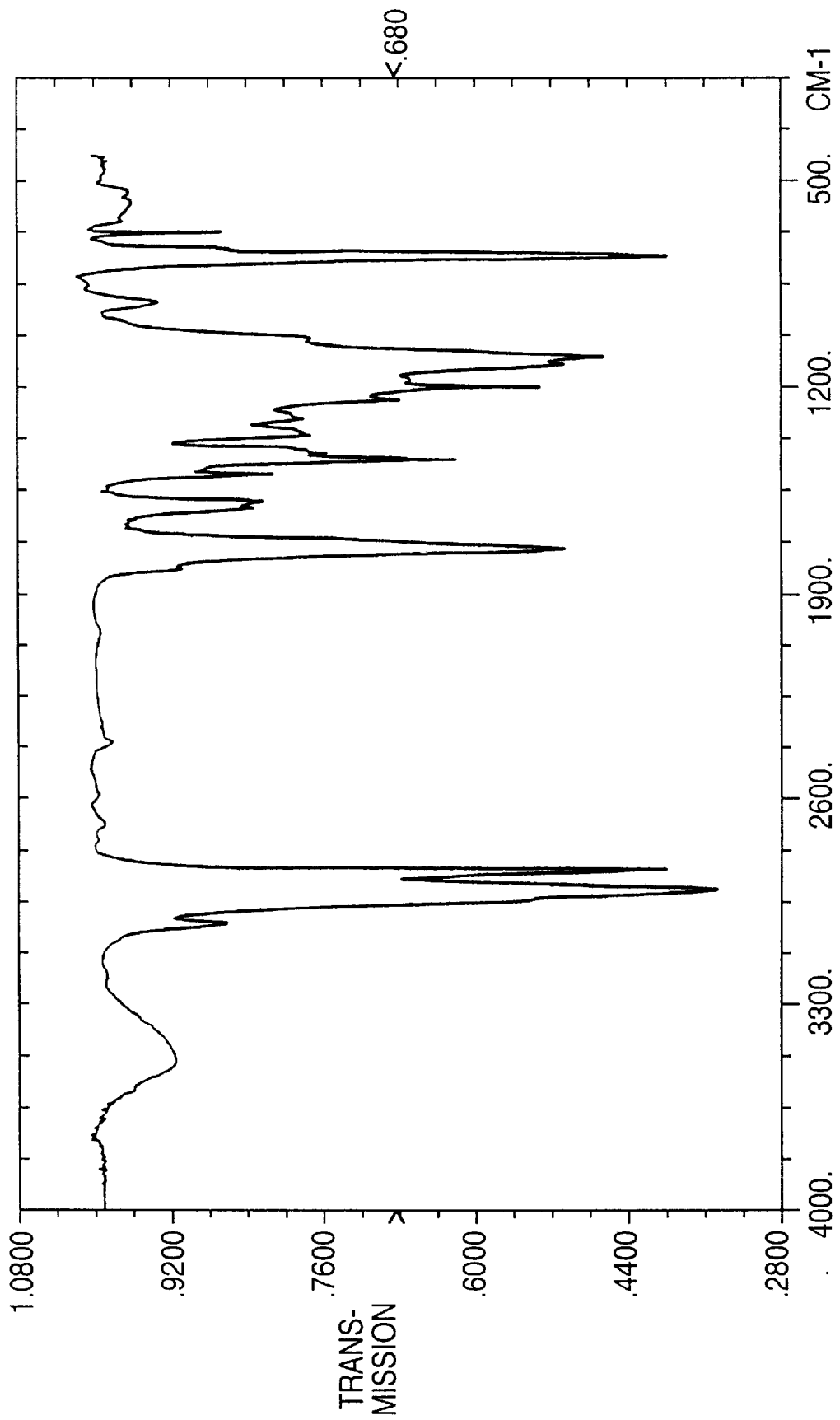
Figure 11:
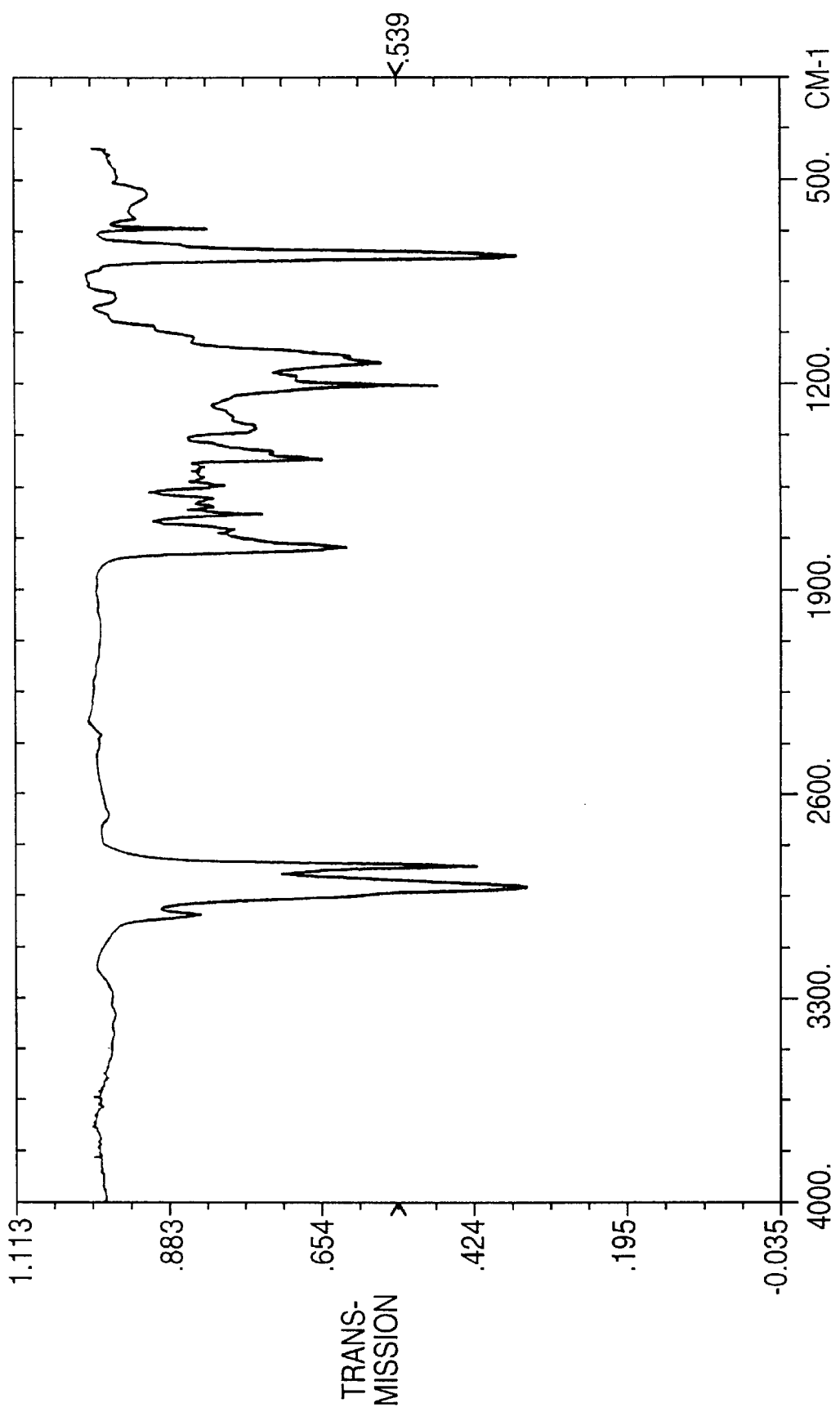
Figure 12:
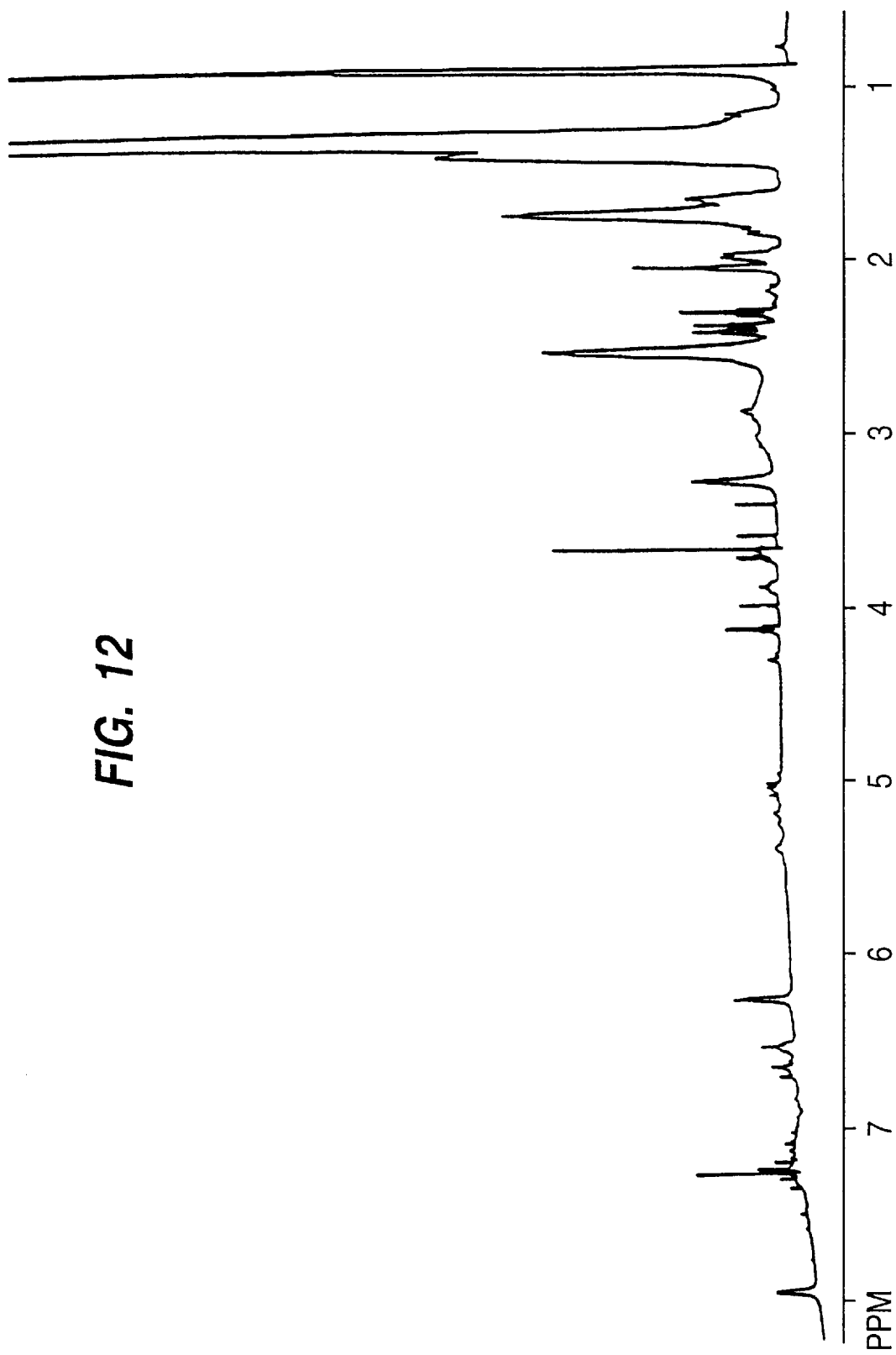
Figure 13:
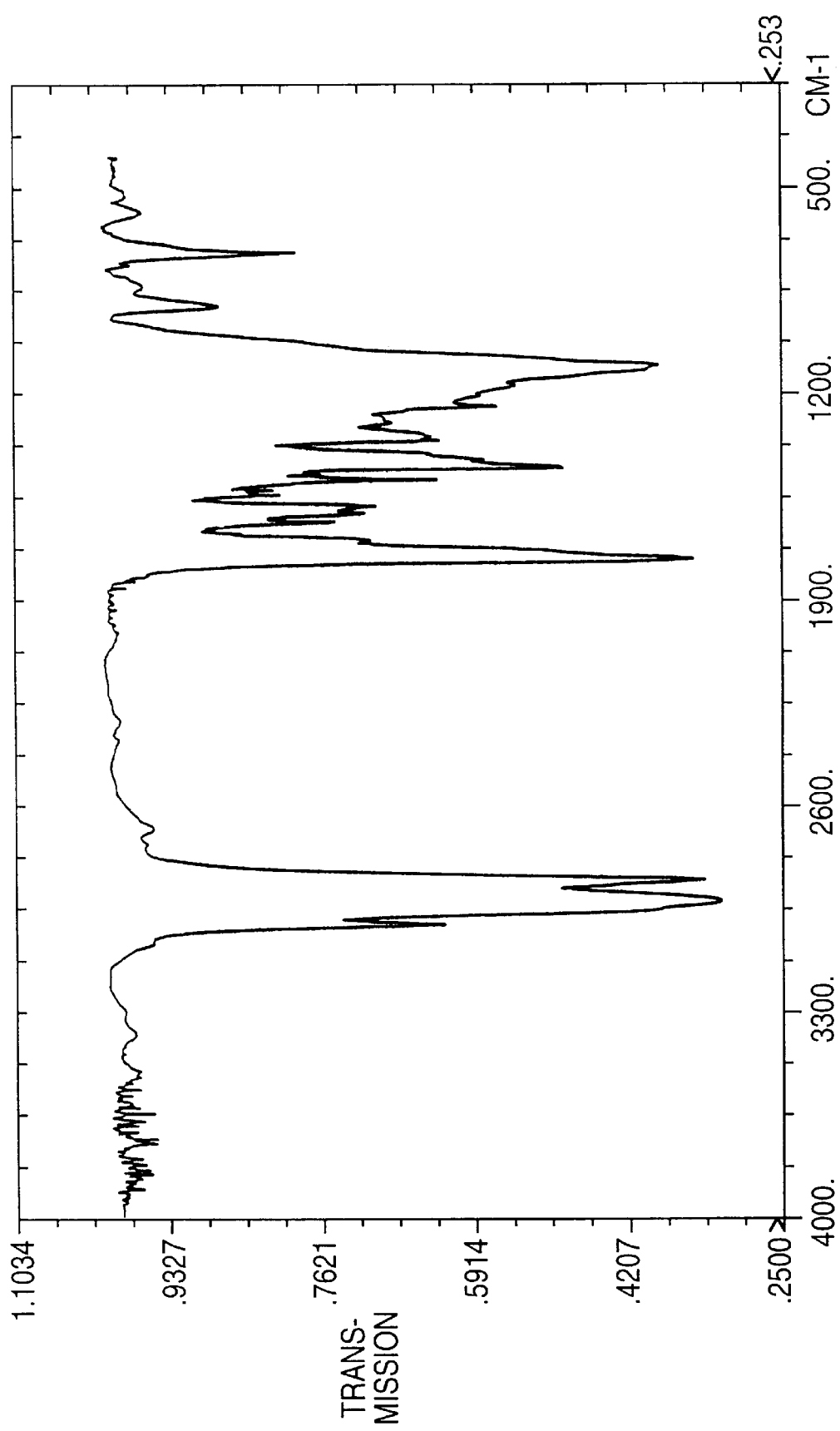

Other characteristics and advantages of the invention will appear in the examples which follow relating to the preparation of OPC peresters and to their use for the development of medicinal products or cosmetic preparations. In these examples, reference is made to FIGS. 1 to 13 which respectively represent:

FIGS. 1 to 6, the UV, IR and one- and two-dimensional $^{13}C$ and $^1H$ NMR spectra of OPC perbutyrate from grape vine, FIGS. 7 and 8, the IR and $^1H$ NMR spectra of OPC perlaurate from grape vine, FIG. 9, the IR spectrum of OPC perpalmitate from grape vine, FIG. 10, the IR spectrum of OPC perlaurate from cluster pine, FIGS. 11 and 12, the IR and $^1H$ NMR spectra of OPC perstearate from green tea, FIG. 13, the IR spectrum of OPC peroleate from grape vine.

Example 1: Preparation of OPC perbutyrate from grape vine.

An OPC fraction as obtained from grape vine according to the method described in Patent FR 1,427,100 (PV No. 998,508) mentioned above is used.

To 10 g of this fraction, dissolved in 200 ml of pyridine and kept stirring, are added dropwise 20 ml of butyryl chloride. The mixture is left stirring, at 70° C., in the absence of air (under a slight flow of nitrogen) and of light for 3 hours. After concentration under reduced pressure, the residue is taken up in 200 ml of chloroform and this organic phase is then washed with twice 250 ml of 0.1N HCl solution, twice 200 ml of distilled water, twice 250 ml of 0.1M $Na_2CO_3$ solution and then three times 200 ml of distilled water. The chloroform phase is recovered, dried over anhydrous $Na_2SO_4$ and filtered, and the solvent is then evaporated off under reduced pressure. The product thus obtained is controlled by spectrometry. The IR and $^1H$ and $^{13}C$ one- and two-dimensional COSY, HMBC and HMMBC NMR spectra are represented respectively in FIGS. 1 to 6.

Example 2: Preparation of OPC pervalerate from green tea.

An OPC fraction as obtained from green tea according to the method described in Patent FR 1,427,100 mentioned above is used.

To 1 g of this fraction, dissolved in 50 ml of pyridine and kept stirring, are added dropwise 3.5 ml of valeric anhydride. The mixture is left stirring, at room temperature, in the absence of air (under a slight flow of nitrogen) and of light for 12 hours. After concentration under reduced pressure, the residue is taken up in 50 ml of chloroform and this organic phase is then washed with twice 50 ml of 0.1N HCl solution, with twice 50 ml of distilled water, with twice 50 ml of 0,1M $Na_2CO_3$ solution and then with three times 50 ml of distilled water. The chloroform phase is recovered, dried over anhydrous $Na_2SO_4$ and filtered, and the solvent is then evaporated off under reduced pressure. The product thus obtained is controlled by spectrometry.

Example 3: Preparation of OPC perhexanoate from grape vine.

To 1 g of OPC from grape vine as mentioned in Example 1, dissolved in 5 ml of pyridine and kept stirring, are added dropwise 4.8 ml of hexanoyl chloride. The mixture is left stirring, at 60° C., in the absence of air (under a slight flow of nitrogen) and of light for 5 hours. After concentration under reduced pressure, the residue is treated as in Example 2. The product thus obtained is controlled by spectrometry.

Example 4: Preparation of OPC perhexanoate from green tea.

To 1 g of OPC from green tea as mentioned in Example 2, dissolved in 20 ml of distilled water, are added 100 ml of 1,2-dichloroethane and the mixture is subjected to vigorous stirring (mechanical stirring at about 1000 revolutions per minute). 100 ml of a buffered aqueous 0.1M solution of sodium phosphate and of sodium hydrogen phosphate (pH in the region of 12.3) are added. 100 mg of tetrabutylphosphonium chloride (phase transfer agent) are added, followed by 2.9 ml of hexanoyl chloride. The mixture is left for 45 minutes under vigorous stirring. At the end of the reaction, the organic phase is recovered and is washed with twice 100 ml of 0.1N sodium hydroxide solution, and then with twice 100 ml of distilled water. The organic phase is recovered and evaporated under reduced pressure. The product thus obtained is controlled by spectrometry.

Example 5: Preparation of OPC persorbate from grape vine.

To 1 g of OPC from grape vine as mentioned in Example 1, dispersed in 50 ml of 1,2-dichloroethane, are added, with stirring, 2.3 g of sorbic acid followed by 4.3 g of dicyclohexylcarbodiimide (DCC). The mixture is left stirring, at room temperature, in the absence of air (under a slight flow of nitrogen) and of light for 2 hours. The organic phase is filtered and the solvent is then removed under reduced pressure. The residue is taken up in 50 ml of hexane. The hexane solution is filtered and then washed with twice 100 ml of 0.1N sodium hydroxide solution, then with twice 100 ml of distilled water. The organic phase is recovered and evaporated under reduced pressure. The product thus obtained is controlled by spectrometry, Example 6: Preparation of OPC perlaurate from grape vine.

To 1 g of OPC from grape vine as mentioned in Example 1, dispersed in 50 ml of dichloromethane, are added, with stirring, 4.2 g of lauric acid followed by 4.3 g of dicyclohexylcarbodiimide (DCC). The mixture is left stirring, at room temperature, in the absence of air (under a slight flow of nitrogen) and of light for 2 hours. The reactive solution is treated as in Example 5. The product obtained is controlled by spectrometry (the IR and $^1$H NMR spectra are represented in FIGS. 7 and 8).

Example 7: Preparation of OPC perlaurate from cluster pine.

An OPC fraction as obtained from cluster pine according to the method described in Patent FR 998,508 mentioned above is used.

To 1 g of this fraction, dissolved in 50 ml of pyridine and kept stirring, are added dropwise 7.8 ml of lauroyl chloride. The reaction is carried out according to the conditions described in Example 2. The product obtained is controlled by spectrometry.

Example 8: Preparation of OPC perpalmitate from grape vine.

50 g of OPC from grape vine as mentioned in Example 1 and 250 ml of pyridine are introduced into a one liter round-bottomed flask, under nitrogen. The mixture is stirred until dissolution is complete. 280 ml of palmitoyl chloride are added slowly (about 1 hour), using a dropping funnel. The reaction is exothermic. The mixture is left stirring for 3 hours. The mixture has then cooled to room temperature, and tends to set solid. 250 ml of chloroform are added and the stirring is continued at room temperature for 12 hours. The solvent is evaporated to dryness under reduced pressure and the residue is then taken up in 1 of chloroform. This solution is washed twice with 500 ml of 1N hydrochloric acid and then twice with 500 ml of distilled water. It is dried over 10 g of calcium sulfate, filtered and then evaporated to dryness under reduced pressure, without exceeding 40° C. The residue is taken up in 500 ml of acetone. The mixture is stirred for the purposes of dispersion (about 1 hour). It is filtered and then dried in a ventilated oven at about 25° C. for 12 hours. About 150 g of product are obtained, which product is controlled by spectrometry (the IR spectrum is represented in FIG. 9).

Example 9: Preparation of OPC perpalmitate from cluster pine.

To 1 g of OPC from cluster pine, as mentioned in Example 7, dissolved in 20 ml of distilled water, are added 100 ml of chloroform and the mixture is then subjected to vigorous stirring (mechanical stirring at about 1000 revolutions per minute). 100 ml of a buffered aqueous 0.1M solution of sodium phosphate and of sodium hydrogen phosphate (pH of the order of 12.3) are added. 120 mg of tetrabutylammonium hydrogen sulfate (phase transfer agent) are added, followed by 5.2 ml of palmitoyl chloride. The mixture is left for 45 minutes under vigorous stirring. At the end of the reaction, the chloroform phase is recovered and is treated according to Example 4. The product thus obtained is controlled by spectrometry (the IR spectrum is represented in FIG. 10).

Example 10: Preparation of OPC perstearate from green tea.

To 1 g of OPC from green tea, as mentioned in Example 2, are added 5 g of stearic acid dissolved in 80 ml of 1,2-dichloroethane. The mixture is stirred. 3.6 g of dicyclohexylcarbodiimide (DCC) are dissolved in 20 ml of 1,2-dichloroethane, and this solution is added to the previous. The mixture is left stirring at room temperature, in the absence of air (under a slight flow of nitrogen) and of light for 15 hours. The reactive solution is treated as in Example 5. The product thus obtained is controlled by spectrometry (the IR and $^1$H NMR spectra are represented in FIGS. 11 and 12).

Example 11: Preparation of OPC perstearate from grape vine.

To 1 g of OPC from grape vine, as mentioned in Example 1, dissolved in 20 ml of distilled water, are added 100 ml of dichloromethane and the mixture is subjected to vigorous stirring (mechanical stirring at about 1000 revolutions per minute). 100 ml of a buffered aqueous solution of sodium phosphate and of sodium hydrogen phosphate (pH in the region of 11), 110 mg of benzyltriethylammonium chloride and then 6.0 ml of stearoyl chloride (in a single portion) are added. The mixture is left for 45 minutes under vigorous stirring. At the end of the reaction, the organic phase is recovered and is treated according to the procedure described in Example 4. The product thus obtained is controlled by spectrometry.

Example 12: Variant for the preparation of OPC perstearate from grape vine.

To 1 g of an oligoprocyanidin (OPC) fraction as mentioned above, dissolved in 100 ml of pyridine and kept stirring, are added dropwise 10.4 g of stearoyl chloride dissolved in 25 ml of pyridine. The mixture is left stirring, at room temperature, in the absence of air (under a slight flow of nitrogen) and of light for 12 hours. After concentration under reduced pressure, the residue is taken up in 100 ml of chloroform and this organic phase is then washed with twice 150 ml of 0.1M HCl solution, with twice 150 ml of distilled water, with twice 150 ml of 0.1M $Na_2CO_3$ solution and then with twice 150 ml of distilled water. The chloroform phase is recovered, dried over anhydrous $Na_2SO_4$ and filtered, and the solvent is then evaporated off under reduced pressure. The residue thus obtained is purified by preparative chromatography on activated silica with a chloroform-0.5% methanol solvent system. The product thus obtained is controlled by spectrometry.

Example 13: Preparation of OPC peroleate from grape vine.

To 1 g of OPC from grape vine as mentioned in Example 1, dispersed in 50 ml of chloroform, are added, with stirring, 6.5 ml of oleic acid followed by 4.3 g of dicyclohexylcarbodiimide (DCC). The mixture is left stirring, at room temperature, in the absence of air (under a slight flow of nitrogen) and of light for 5 hours. The reactive solution is treated as in Example 10. The product obtained is controlled by spectrometry. The IR spectrum is represented in FIG. 13.

Example 14: Preparation of flavanol stearates.

An oligoprocyanidin (OPC) fraction as obtained from grape vine according to the method described in Example 1 is used.

To 1 g of this fraction are added 9 g of stearic acid, 7 g of dicyclohexylcarbodiimide (DCC) and 100 ml of chloroform.

The mixture is maintained at reflux for 24 hours with stirring.

The dicyclohexylurea precipitate formed is removed by filtration. The organic phase is evaporated and the residue is taken up in $CHCl_3$ and subjected to a chromatographic purification.

Example 15: Variant for the preparation of flavanol stearates.

An OPC fraction as obtained above is used.

1 g of such a fraction is reacted with 17.5 g of stearic anhydride or 9.5 g of stearoyl chloride in 100 ml of pyridine. The mixture is maintained at 80° C. for 24 hours with stirring. Most of the pyridine is evaporated off and the remaining phase is taken up in $CHCl_3$. The remaining pyridine is extracted using an aqueous acid solution, and the composition obtained is subjected to a purification by chromatography.

Example 16: Preparation of flavanol oleates.

The process is performed as in Example 15, but replacing the stearic anhydride and stearoyl chloride by the corresponding oleic acid derivative.

Example 17: Preparation of flavanol sorbates.

By working as described in Example 15 but using, as acid derivative, sorbic anhydride or sorbyl chloride, the desired ester is obtained, as demonstrated by 2D NMR analysis.

Example 18: Preparation of flavanol hexanoates.

By working as described in Example 15, but using hexanoic anhydride or hexanoyl chloride, the desired hexanoate is obtained.

Example 19: Antisun cosmetic preparation.

An antisun emulsion having cutaneous anti-ageing properties is prepared by mixing a sunscreen with an ester according to the invention and excipients for cream.

| Neo Heliopan E 1000 ® (isopropyl methoxycinnamate and ethyldiisopropyl cinnamate) | 3% |
|---|---|
| OPC peroleate accoding to Example 13 | 3% |
| Excipients for W/O cream | qs |

Composition of excipients:

| Propylene glycol dicaprylate/dicarate [sic] + stearalkonium hectorite + propylene carbonate (Miglyol 840 gel B ®) | 20.0% |
|---|---|
| Bis-diglyceryl caprylate/caprate/ isostearate/hydroxystearate adipate (Softisan 649 ®) | 5.0% |
| Isostearyl diglyceryl succinate (Imwitor) 780 K ® [sic] | 5.0% |
| Liquid paraffin | 8.0% |
| Solid paraffin | 3.0% |
| Magnesium sulfate | 2.0% |
| Water | qs 100% |

Example 20: Anti-acne cosmetic preparation.

An astringent and antiseptic O/W cream for greasy skin-types is prepared by mixing OPC persorbate according to Example 5, at a proportion of 1%, with an excipient for O/W cream.

The following composition was used as excipient formulation:

| Glyceryl cocoate + hydrogenated cocoa oil + ceteareth-25 (Softisan 601 ®) | 20.0% |
|---|---|
| Glyceryl stearate SE (Imwitor 960 ® flakes) | 8.0% |
| Caprylic/capric/diglyceryl succinate (Miglyol 829 ®) | 5.0% |
| Glyceryl ricineolate [sic] (Softisan 701 ®) | 5.0% |
| Glyceryl laurate (Imwitor 312 ®) | 5.0% |
| Bis-diglyceryl caprylate/cparate/iso-stearate/hydroxystearate adipate (Softisan 649 ®) | 3.0% |
| Silicone oil 344 fluid | 1.0% |
| Water | qs 100% |

Example 21: Preparation of a venotonic and vasculoprotective medicinal product.

Gelatin capsules are prepared from 270 mg of OPC perhexanoate from grape vine (corresponding to 100 mg of OPC) according to Example 3 and from excipients for a gastroresistant coating such as cellulose acetophthalate.

Example 22: Preparation of gelatin capsules for use in dietetics.

OPC perlaurate according to Example 6 is mixed with selenium and vitamin E;

OPC perlaurate: 105 mg (corresponding to 25 mg of OPC)

DL-α-tocopheryl acetate: 40 mg selenium: 50 mg

Example 23: Oral gel which may be used in radio-therapy. The following composition is formulated:

| | |
|---|---|
| 2% Carbopol ® 934 P gel | 89.85 g |
| Methyl para-hydroxybenzoate, sodium salt | 0.13 g |
| Propyl para-hydroxybenzoate, sodium salt | 0.02 g |
| Labrafil ® | 5 g |
| OPC perhexanoate from grape vine according to Example 3 (corresponding to 2 g of OPC from grape vine) | 5 g |

We claim:

1. Polyphenol derivative compositions comprising oligomer or polymer esters containing N+2 monomer moieties, whose monomer moieties correspond to the following formula I:

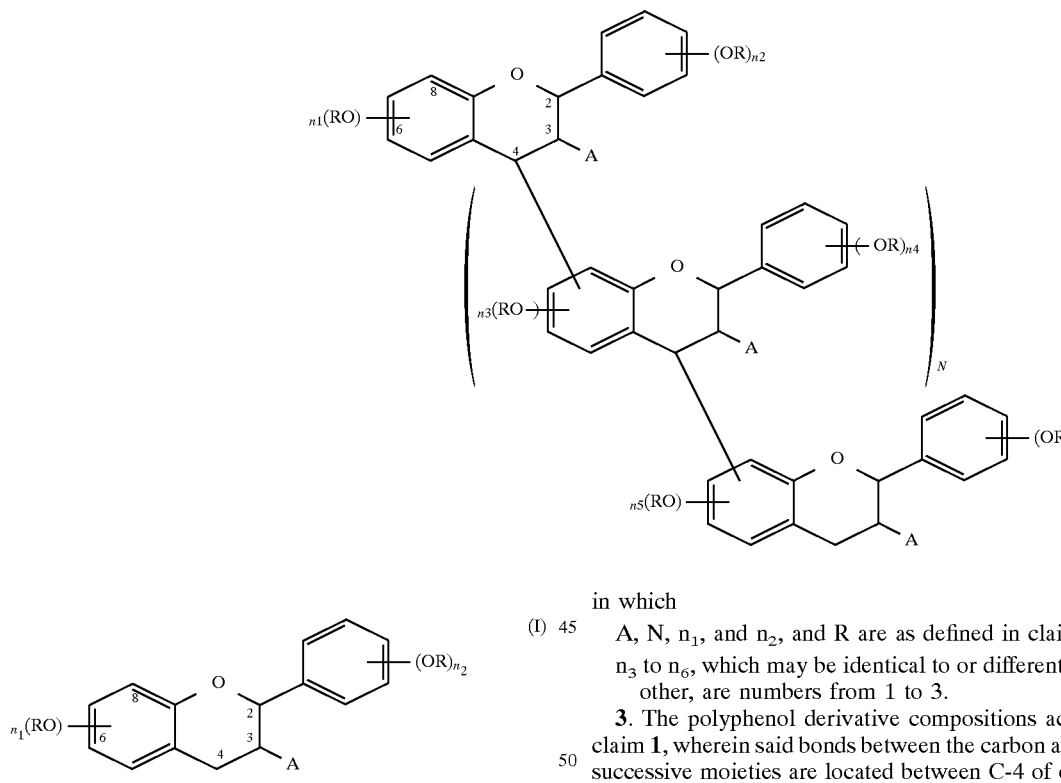

in which

N is a number from 0 to 100,

A represents a group —OR, a hydrogen atom or a substituent R, wherein at least a majority of the substituents R represent a group —$COR_1$, wherein $R_1$ is a saturated or unsaturated, linear or branched alkyl radical of at least two carbon atoms, or an aryl, aralkyl or aralkylene radical, wherein a remainder of the substituents R is a hydrogen atom, an alkyl group, an acyl group —CO—$C_6H_2$—$(OH)_3$, a monosaccharide or a polysaccharide, and $n_1$, and $n_2$, which are identical to or different from each other, are numbers from 1 to 3, corresponding to the number of substitutions on a ring, and the diastereoisomers and the regioisomers of said monomer moieties, whereby said monomer moieties are connected by carbon—carbon bonds or by ether bridges between the rings which make up a flavan ring system.

2. The polyphenol derivative compositions according to claim 1, wherein said oligomers or polymers correspond to the following formula II:

in which

A, N, $n_1$, and $n_2$, and R are as defined in claim 1, $n_3$ to $n_6$, which may be identical to or different from each other, are numbers from 1 to 3.

3. The polyphenol derivative compositions according to claim 1, wherein said bonds between the carbon atoms of the successive moieties are located between C-4 of one moiety and C-6 or C-8 of another moiety.

4. The polyphenol derivative compositions according to claim 1, wherein at least two of the monomer moieties are connected by an ether bridge.

5. The polyphenol derivative compositions according to claim 4, wherein said oligomers and polymers correspond to the following formula III:

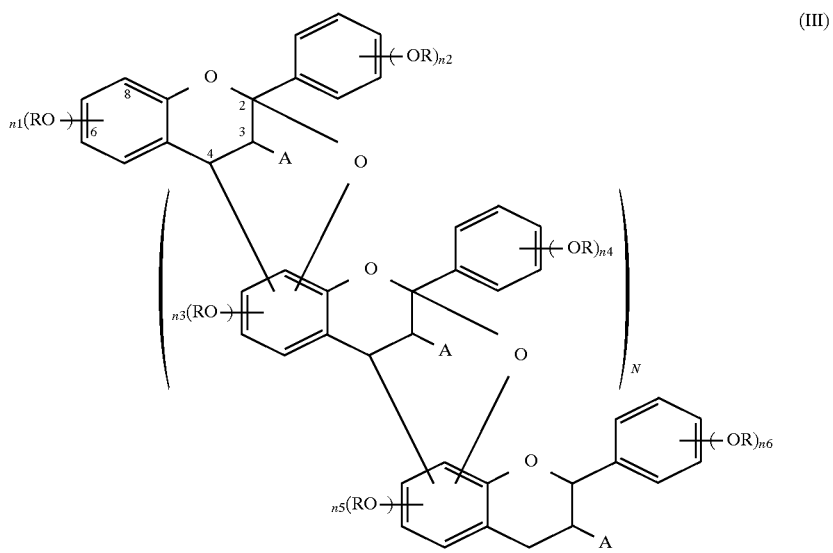

in which A, N, $n_1$, $n_2$, and R are as defined in claim 1, $n_3$ to $n_6$, which may be identical to or different from each other, are numbers from 1 to 3.

6. The polyphenol derivative compositions according to claim 1, wherein N is equal to 0.

7. The Polyphenol derivative compositions according to claim 1, wherein N is a number from 1 to 10.

8. The polyphenol derivative compositions according to claim 1, wherein N is a number from 11 to 100.

9. The polyphenol derivative compositions according to claim 1, wherein $R_1$ represents a saturated or unsaturated fatty acid radical selected from the group consisting of butyric, valeric, hexanoic, sorbic, lauric, palmitic, stearic, oleic, linoleic, linolenic (alpha or gamma), eicosapentanoic, docosahexaenoic or arachidonic acid radicals.

10. The polyphenol derivative compositions according to claim 1, wherein $R_1$ represents a phenyl.

11. The polyphenol derivative compositions according to claim 1, further comprising, as a mixture with said oligomer esters or polymer esters, monomer esters according to claim 1 and esters of monomer moieties according to claim 1.

12. Flavanol derivative compositions comprising oligomers or polymers whose monomer moieties correspond with the following formula I:

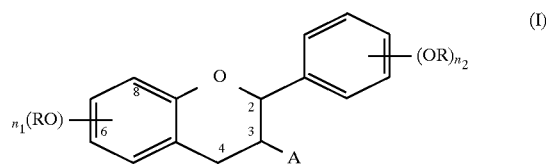

wherein said oligomers or polymers correspond to the following formula II or formula III:

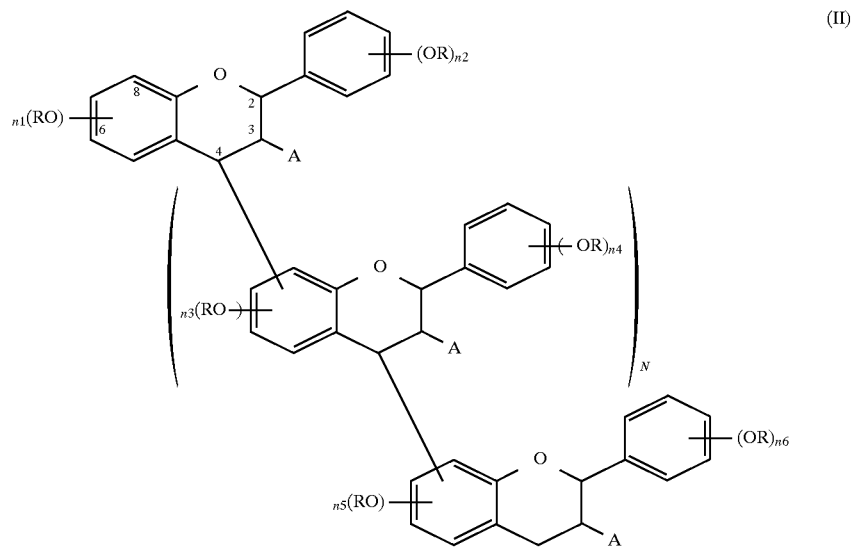

-continued

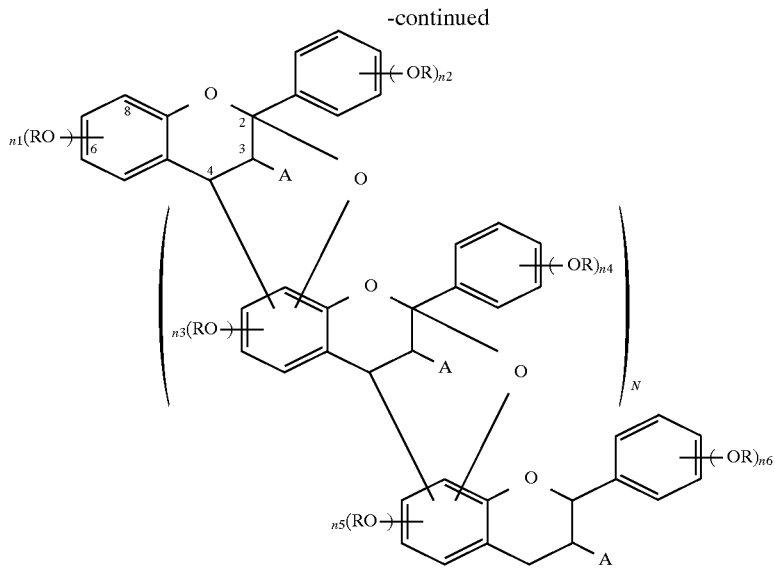

(III)

in which N is a number from 0 to 100, $n_1$ to $n_6$, which may be identical to or different from each other, are numbers from 1 to 3, representing the number of substituents on a benzene ring, A represents a group —OR, wherein at least a majority of the R's represents a group —$COR_1$, wherein $R_1$ is a saturated or unsaturated, linear or branched alkyl radical of at least two carbon atoms, or an aryl, aralkyl or aralkylene radical, and a remainder of the R's represents a hydrogen atom, an alkyl group, an acyl group —CO—$C_6H_2$—$(OH)_3$, a monosaccharide or a polysaccharide.

13. The flavanol derivative compositions according to claim 12, wherein, when the oligomers or polymers correspond to formula III, five oxygen-containing groups per flavanol moiety occupy positions 3, 5, 7, 3' and 4', respectively, to form esters, at least two of which oxygen containing moieties are connected by an ether bridge between C-2 and one of the carbons, $C_5$ to $C_8$.

14. A process for the synthesis of polyphenol derivative compositions according to claim 1, comprising the step of reacting said phenol compositions having at least one free —OH group with an acylating agent capable of providing an acyl radical —$COR_1$ as defined in claim 1, to substitute said at least one free —OH group with the acyl radical —$COR_1$.

15. The process according to claim 14, wherein an acid $R_1COOH$ or a derivative of such acid is used as the acylating agent.

16. The process according to claim 15, wherein when $R_1COOH$ is used as the acylating agent, the reaction is performed in the presence of an acid-activating agent.

17. The process according to claim 14, wherein the reaction is carried out in the presence of a solvent which allows partial solubilization of the phenol compositions.

18. The process according to claim 14, wherein the reaction with the acid derivative is performed in aqueous alkaline medium, according to the Schotten Baumann reaction.

19. Pharmaceutical preparations, comprising an effective amount of at least one composition according to claim 1, in combination with an inert vehicle which is suitable for a pharmaceutical application.

20. Cosmetic preparations, comprising at least one composition according to claim 1, in combination with an inert vehicle which is suitable for a cosmetic application.

21. A method of using the compositions according to claim 1, in dietetics.

22. The polyphenol derivative compositions according to claim 1, wherein $R_1$ represents aralkyl.

23. The polyphenol derivative compositions according to claim 1, wherein $R_1$ represents benzyl.

24. The polyphenol derivative compositions according to claim 1, wherein $R_1$ represents styryl.

25. The process according to claim 14, wherein the acid derivative is an acid halide.

26. The process according to claim 25, wherein the acid halide is acid chloride.

27. The process according to claim 14, wherein the acid derivative is an anhydride.

28. The process according to claim 14, wherein the acid derivative is an ester.

29. The process according to claim 15, wherein the acid-activating agent is one of dicyclohexylcarbodiimide and tert-butylchoroformate.

30. The process according to claim 16, wherein the solvent is one of a halogenated derivative and an amine.

31. The process according to claim 30, wherein the halogenated derivative is one of dichloromethane, chloroform and 1,2-dichloromethane.

32. The process according to claim 30, wherein the amine is pyridine.

* * * * *